United States Patent [19]
Self et al.

[11] Patent Number: 5,989,851
[45] Date of Patent: Nov. 23, 1999

[54] METHOD FOR ENHANCING SHELF LIFE OF BIOLOGICAL GROWTH MEDIA

[75] Inventors: Jim Self, San Jose; Robert D. Hall; Daniel R. Webster, both of Sunnyvale, all of Calif.

[73] Assignee: BioMed Diagnostics, San Jose, Calif.

[21] Appl. No.: 08/922,144

[22] Filed: Aug. 25, 1997

Related U.S. Application Data

[63] Continuation-in-part of application No. 08/242,014, May 12, 1994, Pat. No. 5,661,029.

[51] Int. Cl.$^6$ ........................................................ C12Q 1/24
[52] U.S. Cl. .............................. 435/30; 435/34; 435/383; 435/395; 435/420
[58] Field of Search .............................. 435/29.3, 32, 34, 435/325, 383, 395, 410, 420

[56] References Cited

U.S. PATENT DOCUMENTS

| | | | |
|---|---|---|---|
| 3,726,767 | 4/1973 | White | 195/127 |
| 4,271,270 | 6/1981 | Lukaesek | 435/294 |
| 4,396,717 | 8/1983 | Fjebig et al. | 435/301 |
| 4,867,316 | 9/1989 | Rollender et al. | 206/670 |
| 5,173,298 | 12/1992 | Meadows | 424/427 |
| 5,417,576 | 5/1995 | Hill | 435/299 |
| 5,661,029 | 8/1997 | Self et al. | 435/288.3 |

*Primary Examiner*—David A. Redding
*Attorney, Agent, or Firm*—Wilson Sonsini Goodrich & Rosati

[57] ABSTRACT

A method for prolonging the shelf life of biological growth media provides a device with a tray for growing and observing a microbiological culture. The device includes a substrate with a well to provide a containment and barrier for the biological growth medium to grow an organism in the tray and a lid that is sealable and resealable around the substrate periphery. The lid includes an interior side that sheets out upon condensation of vapor and faces the growth medium. A barrier layer is positioned over the well. The biological growth media is introduced in the well and the lid around the substrate periphery is sealed.

7 Claims, 4 Drawing Sheets

FIG. — 1

METHOD FOR ENHANCING SHELF LIFE OF BIOLOGICAL GROWTH MEDIA

This application is a continuation-in-part of application Ser. No. 08/242,014 filed May 12, 1994, now U.S. Pat. No. 5,661,029, by inventors Jim Self, Robert D. Hall and Daniel R. Webster, which application is incorporated herein by reference in its entirety.

BACKGROUND OF THE INVENTION

1. Field of the Invention

This invention relates generally to biological growth media, and more particularly to biological growth media that are subject to oxidation or dehydration.

2. Description of Related Art

Growth media are used for a variety of different organisms, including but not limited to fungi, bacteria, protozoa, and the like, in order to grow a microbiological sample in the medium. The biological culture is permitted to grow in or on the growth medium, and it is then observed for identifying characteristics.

Currently, this is generally performed in a test tube with the growth medium in the tube on a slant. A variety of media is used. One example of a class of growth media is the dermatophytes test medium which include color change agents. As soon as the biological sample affects the medium the medium begins to change color. The microbiologist then removes the biological sample from the tube and spreads it on a growth medium located on a glass slide. A glass cover slip is positioned over the biological sample, permitting the biological sample to grow. After identifiable growth occurs, the biological sample is treated with phenyl cotton blue so it does not become contagious. This kills the biological sample, but it is still observable. The growth sample is then removed from the medium and observed with a microscope.

One of the difficulties with this method is that as the biological sample grows, an identifying structure, a very delicate flowering portion of the dermatophyte or fungi, grows and it is easy to destroy. Merely breathing on it can destroy it.

Removal of such a biological sample with its delicate identifying structure from a device adapted for growth, to a device that is suitable for observation, presents numerous problems. There are too many opportunities to damage the sample, making it difficult, or impossible to observe and therefore characterize. This method, and devices associated with this method, are unreliable, unpredictable, time consuming and expensive.

There is a need for a method that permits the growth, transportation and observation of the delicate biological structures while minimizing damage to the biological structure. There is a further need for a method for enhancing shelf life of a biological growth media.

SUMMARY OF THE INVENTION

It is an object of the invention to provide a method for enhancing the shelf life of a biological growth media.

It is another object of the invention is to provide a method for enhancing the shelf life of a biological growth media that is sensitive to oxidation or dehydration.

Yet another object of the invention is to provide a method for enhancing the shelf life of a biological growth media up to three years.

A method for prolonging the shelf life of biological growth media provides a device with a tray for growing and observing a microbiological culture. The device includes a substrate with a well to provide a containment and barrier for the biological growth medium to grow an organism in the tray and a lid that is sealable and resealable around the substrate periphery. The lid includes an interior side that sheets out upon condensation of vapor and faces the growth medium. A barrier layer is positioned over the well. The biological growth media is introduced in the well and the lid around the substrate periphery is sealed.

DETAILED DESCRIPTION OF THE PREFERRED EMBODIMENTS

Figure 1:
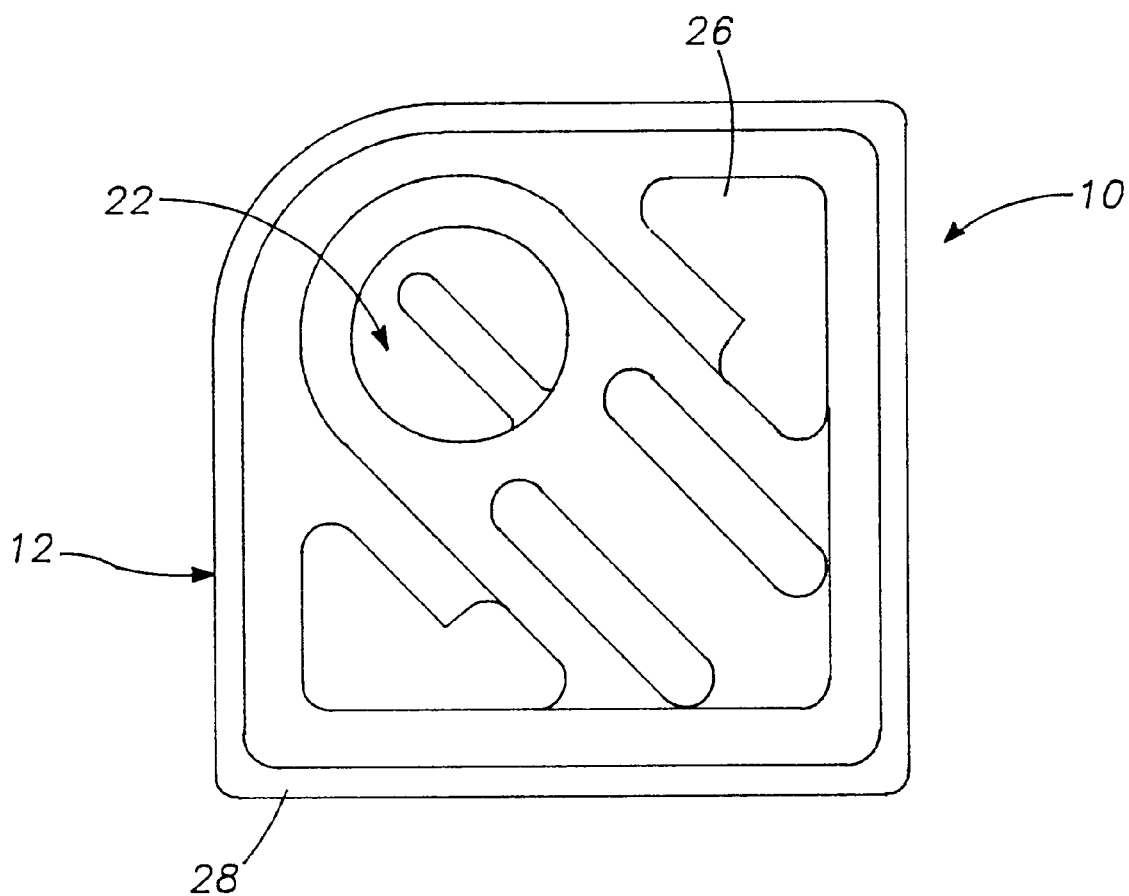
FIG. 1 is a plan view of the biological culture growth and observation system according to the present invention.
Figure 2:
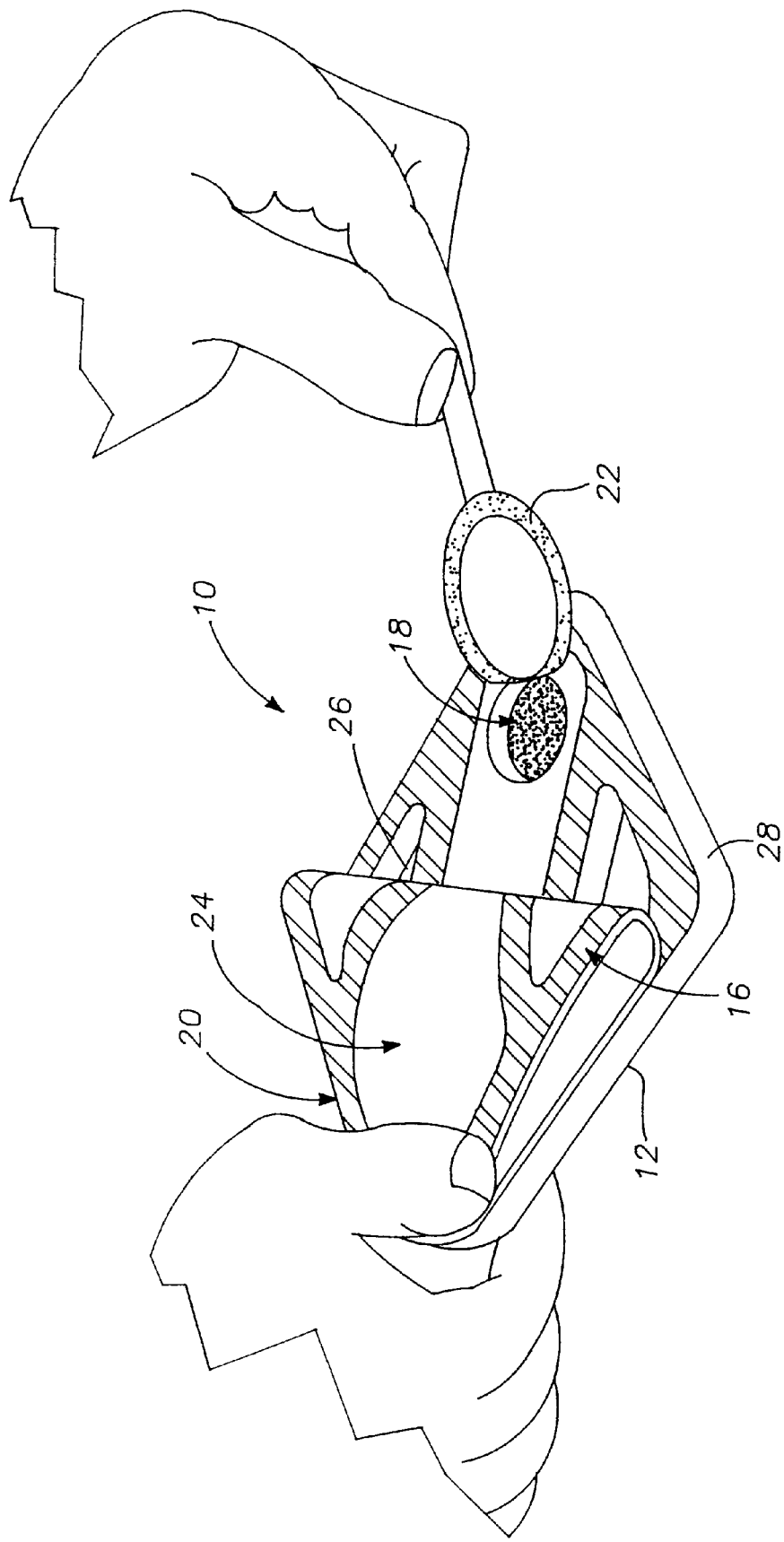
FIG. 2 is a perspective view of the biological culture growth and observation system with the lid pulled back according to the present invention.
Figure 3:
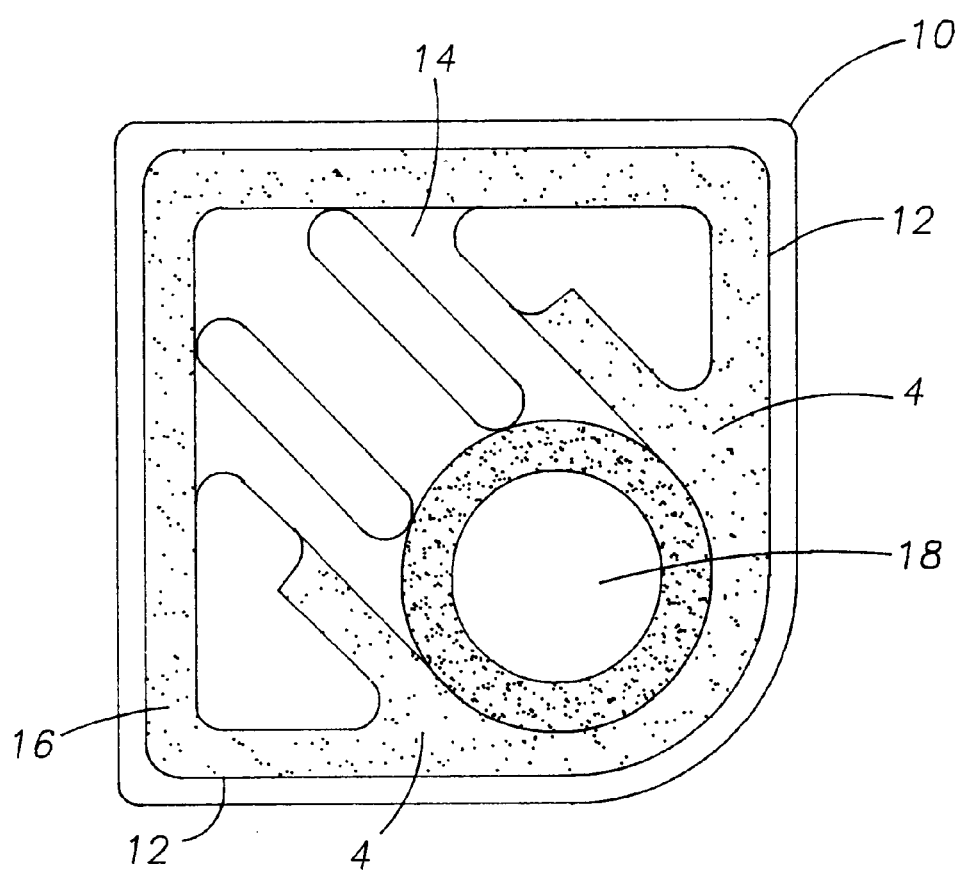
FIG. 3 is a top down view of the biological culture growth and observation system according to the present invention.

Referring now to FIGS. 1 and 2, a biological culture growth and observation system 10 includes a tray 12 with a top 14 that includes a sealable section 16. A depression or well 18 (FIG. 3) is included in tray 12 to receive a growth medium, not shown, to grow any variety of organisms in well 18. Well 18 can be formed as an integral part of tray 12 or it can be a separate section that is attached to tray 12. Well 18 includes both side and bottom walls. It will be appreciated that well 18 may take a variety of forms, including but not limited to, (i) a single flat bottom depression, (ii) a depression with an adjoining raised area, (iii) a flat surface covered with a thin film of growth medium, (iv) a multi-cavity depression wherein each cavity holds a distinct medium and (v) a multi-cavity depression in which each cavity holds a distinct growth medium and there is another medium over the entire multi-cavity depression.

Any number of different biological organisms can be grown in well 18 including but not limited to fungi bacteria, yeast and the like. It will be appreciated that the invention is not limited to these specific biological organisms.

A lid 20, that is both sealable and resealable around sealable section 16, is included. Lid 20 has an interior side 24, shown in FIG. 2, that faces the growth medium in well 18 but does not fog up upon vapor condensation. When a biological sample is placed in a culture medium in well 18, vapors can be created. Interior side 24 is either a coated material such as Vistex-75, available from Film Specialties, Inc. Whitehorn, N.J., or lid 20 is formed of a material that does not permit fogging. Both sides of lid do not have to meet this requirement, only interior side 24 must possess the non-fogging properties.

Figure 4:
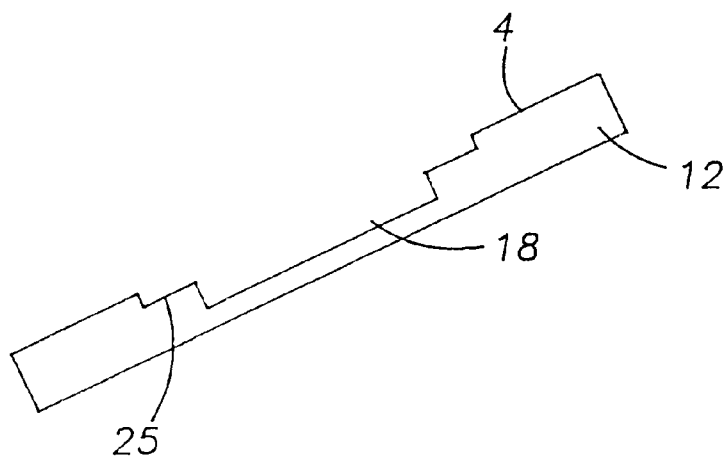
FIG. 4 is a sectional view of the biological culture growth and observation system, taken along the lines 4—4 in FIG. 3 according to the present invention.

A barrier layer 22 is positioned over well 18 to minimize evaporation from the growth medium. Barrier layer 22 is initially positioned over well 18 on a shoulder 25 (FIG. 4) in a manner so that the culture medium does not dry out while biological culture growth and observation system 10 is stored. A suitable barrier layer is available from LamaShield, Product No. 8034, Cleveland, Ohio. Barrier layer 22 can also include a tab which the operator pulls in order to remove barrier layer 22 from the top of well 18. Barrier layer 22 is removed just before the biological sample is added to the culture medium. Lid 20 is first pulled back in a direction away from tray top 14 in an amount sufficient so that barrier layer 22 can be removed, and the biological sample added to the culture medium. Barrier layer 22 is then discarded, and lid 20 is then again sealed to tray top 14 at sealable section 16. It should be noted that sealable section 16 can be at the peripheral edge of tray top 14, or it may on any area of tray top 14. In certain applications air passages 26 are included and formed between tray top 14 and lid 20 when the two are sealed together. Air passages introduce a gas, including but not limited to air or $CO_2$, that promotes the growth of the bacterial sample in the culture medium.

Biological culture growth and observation system 10 is designed so that the biological sample can grow up and spread across the surface of the culture medium, and in certain instances spread across portions of tray top 14, possibly reach interior side 24 of lid 20, and may even grow right on interior side 24. The grown biological sample is identified by its structure and is viewed through a microscope objective. In many instances, microscopic structures will be the point of discrimination. There is a point where it is possible to discriminate the biological sample after it has grown. This is done visually through the use of a microscope. With dermatophytes, there may be a color change in the culture medium. It will be appreciated that the present invention is applicable to a variety of different microscopes and powers. Lid 20 must be thinner than the working distance between the objective lens and the object to be viewed Significantly, biological culture growth and observation system 10 performs two functions in one device. It cultures and identifies a biological sample. It also serves as its own transport device, observation platform, growth platform, and as a single disposal unit for the biological sample, culture medium and the substrate on which all of this takes place.

The amount of biological sample placed in well 18 can be in the milligram range. Only a small amount of biological sample may be necessary such as but not limited to, two or three hair follicles, a piece of a toe nail, or a simple skin scrapping. It can be a single organism, or thousands of organisms.

Biological culture growth and observation system 10 reduces an operator's exposure to the biological sample. There are certain biological samples that can be hazardous to humans. Biological culture growth and observation system 10 does not require the transfer of the culture medium with the biological sample to a slide, and thus is a device that performs two functions and reduces operator exposure.

The present invention is suitable for substantially any culture medium that supports the growth of the biological organism. Such culture media are well known to those skilled in the art.

Tray 12 is made of a material that provides sufficient support for the culture medium and the growth of the biological organism in well 18, It is preferably thermally formable, optically transparent in order to transmit light, non reactive with the culture medium and does not permit the transport of oxygen or water vapor. Suitable materials include glasses, plastics including but not limited to Polystryene, PETG, Polypropolene, and the like. Accordingly, the bottom of well 18 is also optically transparent.

In one embodiment, tray 12 has an outer trim dimension of about 3.25 inches, a height of about 0.25 inches that is created by an underside lip 28, the bottom of well 18 to the top of tray 12 is 0.14 inches, the depth of well 18 is about 0.12 inches and the diameter of well 18 is 1 inch. It will be appreciated that there are any number of variations to these dimensions, and the present invention is not to be limited by any or all of the dimensions. Well 18 must be thin enough so that light can penetrate through it and the growth medium in order for an operator to view the grown biological organism through a microscope objective. Lid 20 may dimensionally extend beyond tray top 14 to facilitate the ability to pull lid 20 away from tray top 14.

Lid 20 is made of a material combination/lamination that is capable of being resealed to sealable section 16, has optical transparency, is nontoxic to biological organisms, and has interior side 24 that does not fog up. Suitable materials include optically transparent plastics including but not limited to polyurethane, PET, PP, Polypropolyene and the like.

The seal formed between lid 20 and sealable section 16 must be sufficient that organisms do not migrate out of biological culture growth and observation system 10. The seal may be a microbial barrier, but it is not necessary that it be of this nature.

Lid 20 and tray top 14 can be sealed in a number of ways. An adhesive can be employed such as acrylic based adhesives. Suitable adhesives include but are not limited to 3M 9374, available from 3M. Lid 20 can also be mechanically sealed, sealed by a thermal bond, or even welded with the use of a layer of solvent. The solvent can be placed on lid 20 or tray top 14, and then become dissolved in order to create the weld.

Figure 5:
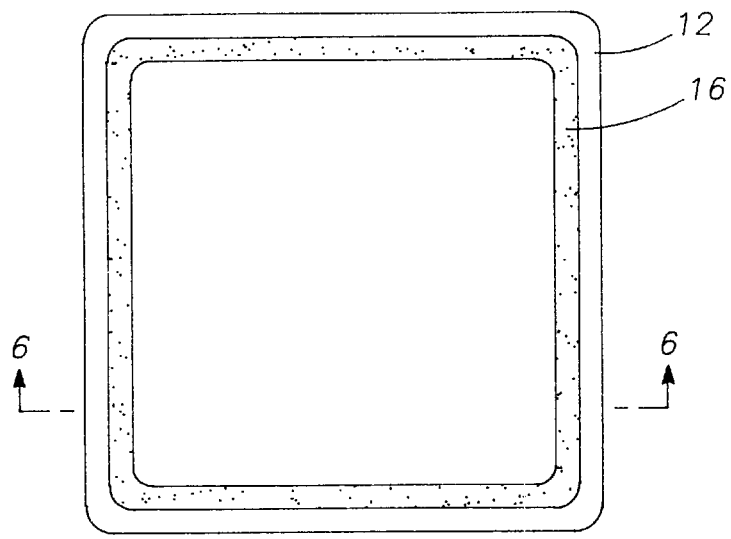
FIG. 5 is a top down view of the resealable lid with a mechanical closure according to the present invention.
Figure 6:
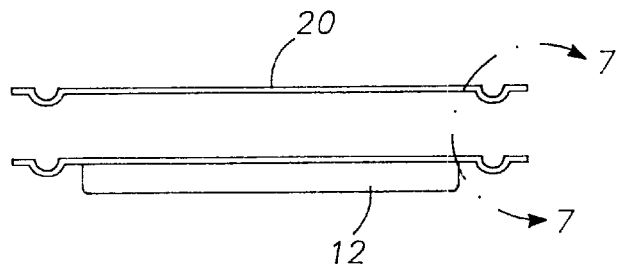
FIG. 6 is a sectional view of the resealable lid with the mechanical closure taken along the lines 6—6 of FIG. 5 according to the present invention.
Figure 7:
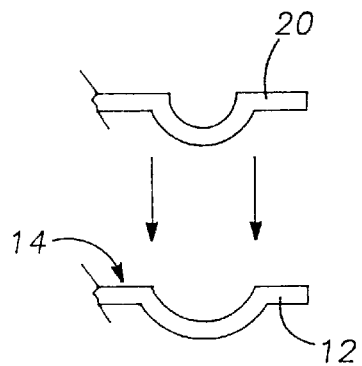
FIG. 7 is a detailed sectional view of the lid and the tray, with a frictional fit mechanical closure, according to the present invention.

FIGS. 5 through 7 illustrate a mechanical interlock seal between lid 20 and tray 12. The two are engaged in a friction fit to form a mechanical closure.

In one embodiment lid 20 can include or incorporate an optical lens.

Biological culture growth and observation system 10 provides long shelf life of up to one, year, two years, three years or more for a variety of base media and antibiotic additives. System 10 has a high barrier to oxygen and water transport and provides long shelf life for antibiotic additives that are subject to oxidation or dehydration. System 10 also provides for room temperature storage, visible growth observation, microscope inspection of morphology. In various embodiments well 18 have a one inch diameter in the three inch square package, a two inch diameter in a three or four inch square package, and the like.

A variety of different base media can be used including but not limited to Sabouraud Dextrose Agar, Potato Dextrose Agar, Corn Meal Agar, Potato Flake Agar, Blue Corn Meal Agar and the like.

A variety of different antibiotic additives can be used and packaged with the long shelf life including but not limited to amphotericin, chloramphernical, cycloheximide, colisten, gentamycin, ketocanozole, lincomycin, metronidazole, nystatin, polymixin, trimethoprim, vancomycin and the like.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

We claim:

1. A method for storing an antibiotic additive, comprising:
   providing a device with a tray for growing and observing a microbiological culture, the device including a substrate with a well to provide a containment and barrier for a growth medium to grow an organism in the tray, a lid that is sealable and resealable around the substrate periphery, the lid including an interior side that sheets out upon condensation of vapor and faces the growth medium, and a barrier layer positioned over the well;
   introducing the antibiotic additive in the well; and
   sealing the lid around the substrate periphery.

2. The method of claim 1, wherein the antibiotic additive includes a base media.

3. The method of claim 2, wherein the base media is selected from the group consisting of, Sabouraud Dextrose Agar, Potato Dextrose Agar, Corn Meal Agar, Potato Flake Agar and Blue Corn Meal Agar.

4. The method of claim 1, wherein the antibiotic additive is selected from the group consisting of, amphotericin, chloramphernical, cycloheximide, colisten, gentamycin, ketocanozole, lincomycin, metronidazole, nystatin, polymixin, trimethoprim and vancomycin.

5. The method of claim 1, wherein the antibiotic additive has a shelf life of at least one year.

6. The method of claim 1, wherein the antibiotic additive has a shelf life of at least two years.

7. The method of claim 1, wherein the antibiotic additive has a shelf life of at least three years.

* * * * *